United States Patent [19]

Wegman et al.

[11] Patent Number: 4,670,570
[45] Date of Patent: Jun. 2, 1987

[54] PRODUCTION OF CARBOXYLIC ACIDS FROM ALCOHOLS USING RHODIUM COMPLEX CATALYSTS

[75] Inventors: Richard W. Wegman, South Charleston; Anthony G. Abatjoglou, Charleston, both of W. Va.

[73] Assignee: Union Carbide Corporation, Danbury, Conn.

[21] Appl. No.: 891,065

[22] Filed: Jul. 31, 1986

Related U.S. Application Data

[60] Continuation of Ser. No. 729,419, May 1, 1985, abandoned, which is a division of Ser. No. 633,021, Jul. 20, 1984.

[51] Int. Cl.$^4$ .............................................. C01F 15/00
[52] U.S. Cl. ...................................... 556/18; 560/232
[58] Field of Search .......................................... 556/18

[56] References Cited

U.S. PATENT DOCUMENTS

| | | |
|---|---|---|
| 1,697,109 | 1/1929 | Dreyfus . |
| 2,508,513 | 5/1950 | Groombridge . |
| 3,060,233 | 10/1962 | Hohenschutz . |
| 3,769,329 | 10/1973 | Paulik et al. . |
| 3,798,267 | 3/1974 | Wakmatsu et al. . |
| 4,102,920 | 7/1978 | Bartish ................. 260/532 |
| 4,194,056 | 3/1980 | Antoniades . |
| 4,212,989 | 7/1980 | Isshiki et al. . |
| 4,374,278 | 2/1983 | Bryant et al. ........... 260/429 R X |
| 4,400,548 | 8/1983 | Abatjoglou et al. ........... 260/429 R |
| 4,473,505 | 9/1984 | Mitchell, III ............ 260/429 R X |
| 4,491,675 | 1/1985 | Abatjoglou et al. ........... 260/429 R |

FOREIGN PATENT DOCUMENTS

| | | |
|---|---|---|
| 0018927 | 11/1980 | European Pat. Off. . |
| 0045637 | 2/1982 | European Pat. Off. . |
| 0097978 | 1/1984 | European Pat. Off. . |
| 0144935 | 6/1985 | European Pat. Off. . |
| 0144936 | 6/1985 | European Pat. Off. . |
| 2317269 | 2/1977 | France . |
| WO80/01690 | 8/1980 | PCT Int'l Appl. ............. 260/429 R |
| 1286224 | 8/1972 | United Kingdom . |
| 1293193 | 10/1972 | United Kingdom . |
| 1584740 | 2/1981 | United Kingdom . |

OTHER PUBLICATIONS

W. Hieber and R. Kummer artile in "Chem. Ber.", vol. 100, pp. 148-159 (1967).
International Search Report PCT/US 85/01359.

Primary Examiner—Helen M. S. Sneed
Attorney, Agent, or Firm—Eugene C. Trautlein

[57] ABSTRACT

A process for the production of organic carboxylic acids by the catalytic reaction of an alcohol and, carbon monoxide in contact with a homogeneous catalyst system of rhodium metal atom, a phosphorus containing ligand in which there is present at least one oxo oxygen atom attached to a phosphorus atom or a carbon atom to form a Z group and the

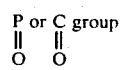

in said Z group is located at least one carbon atom removed from the phosphorus atom of the molecules represented by the formulas

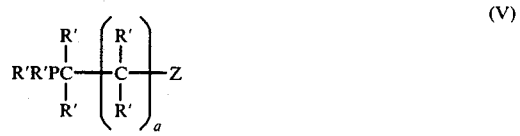

(V)

or

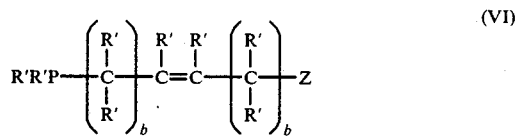

(VI)

and a halogen promoter, under mild reaction conditions, wherein R' is aryl, alkaryl, aralkyl or alkyl, and wherein 1 or more of said R' groups can be substituted with a Z group but not more than 3 of said R' groups in the molecule are so substituted; a is an integer from 0–4; b is an integer from 0–3; and Z is P(O)R'R'; —C(O)OR" or C(O)R", wherein R" is R' or —H.

12 Claims, No Drawings

PRODUCTION OF CARBOXYLIC ACIDS FROM ALCOHOLS USING RHODIUM COMPLEX CATALYSTS

This application is a continuation of prior U.S. application Ser. No. 729,419, filed May 1, 1985, abandoned, which is a division application of prior U.S. application Ser. No. 633,021, filed July 20, 1984.

BACKGROUND OF THE INVENTION

The production of organic compounds using synthesis gas, which is a mixture of carbon monoxide and hydrogen, or from carbon monoxide as one of the reactants has been known for a significant period of time. It is well known that one can produce methanol directly from synthesis gas and that methanol can be further reacted by hydroformylation, homologation and carbonylation reactions to produce acetaldehyde, ethanol and acetic acid or its methyl ester, respectively. It is also known that alcohols, esters, ethers, and other organic compounds can be reacted with synthesis gas or carbon monoxide to produce oxygenated organic compounds. The difficulties, however, have resided in the ability to carry out any one of these chosen reactions to produce the desired compound at acceptable efficiency, conversion rate and selectivity.

In almost all instances the reaction is generally catalyzed using a Group VIII transition metal compound as the catalyst and a halogen as the promoter. It is known that many other metal compounds and promoters can be used. In addition, the prior art has disclosed the use of secondary activators or ligands in conjunction with the metal catalysts and promoters. These secondary activators can be other metallic salts or compounds, amines, phosphorus compounds, as well as a multitude of other compounds that have been disclosed in the published literature. Thus, a typical catalyst system contains the metal atom catalyst, promoter and, optionally, ligands, solvents and secondary activators. Though a significant amount of literature does exist describing the production of acetic acid, to our knowledge it does not disclose or suggest our invention. Several of the pertinent patents in this area are discussed below.

French Pat. No. 2,317,269, filed by Compagnie Des Metaux Precieux and published on Feb. 4, 1977, discloses the production of aliphatic carboxylic acids by the reaction of an alcohol with carbon monoxide in the presence of a catalyst containing at least three essential components, iridium atom, copper atom and halogen. This is not our process.

In European Patent Application No. 0018927; filed by Gauthier-Lafaye et al on Apr. 23, 1980 and published on Nov. 12, 1980, there is described a process for the production of monocarboxylic acids by the carbonylation of an alcohol using a nickel catalyst, a halide and a solvent. In this reference synthesis gas is used. In the instant process an organic acid is produced from an alcohol and carbon monoxide using a rhodium complex as the catalyst.

In European Patent Application No. 0045637, filed by Pruett on July 31, 1981 and published on Feb. 10, 1982, there is disclosed the direct conversion of formic acid esters to their corresponding carboxylic acids without the presence of carbon monoxide, using as the catalyst a soluble iridium salt and an iodine promoter. This is not the present process.

Another known procedure for producing acetic acid is the catalytic isomerization of methyl formate as shown by the reaction:

$$CH_3OOCH \rightarrow CH_3COOH$$

This procedure is shown in U.S. Pat. No. 1,697,109, issued to Henry Dreyfus on Jan. 1, 1929. The process described is a vapor phase isomerization reaction carried out at 200° C. to 450° C. at a pressure, for example, on the order of 200 atmospheres using a metal oxide or acetate catalyst. That is typical of the extreme reaction conditions normally used in this area of technology. The reference does not disclose the use of alcohols as starting materials.

U.S. Pat. No. 2,508,513, assigned to Celanese Corporation and issued on May 23, 1950 claims a Group VIII metal atom based catalyst, e.g. nickel, promoted with methyl iodide for the isomerization of methyl formate to acetic acid, carried out at 300° C. to 400° C. and at a pressure up to 6000 psig. Carbon monoxide may be present. It does not disclose the production of organic carboxylic acids from mixtures of an alcohol and carbon monoxide. Nor does it disclose the use of the rhodium complex catalyst of the present invention at low reaction temperature and pressure.

U.S. Pat. No. 3,060,233, issued to Hohenschutz on Oct. 23, 1962, discloses the carbonylation of methanol to acetic acid using a metal of the iron group of the Periodic Table and a halide. It does not disclose use of the instant rhodium complex at the mild pressure and temperature conditions employed herein.

U.S. Pat. No. 3,769,329, issued Oct. 30, 1973 to Paulik et al, discloses the use of a conventional rhodium catalyst and conventional ligands. The preferred mode of operation of this prior art process requires a large excess of water to ensure selectivity to acetic acid. This reference employs relatively extreme reaction conditions of temperature and pressure, and makes no distinction relating to the suitability of useful ligands.

U.S. Pat. No. 3,798,267, issued Mar. 19, 1974, relates to the conversion of methyl formate to acetic acid in the presence of a catalyst system consisting essentially of activated carbon and a halogen promoter. The reference uses catalyst and starting materials different than those employed in the invention of this application.

U.S. Pat. No. 4,194,056, filed by Antoniades and issued Mar. 18, 1980, discloses the production of carboxylic acid from methyl formate using a soluble rhodium catalyst, halogen promoter and carbon monoxide. This is not the process of the instant invention, nor does this reference disclose or suggest the use of a specific rhodium complex nor the instant mild reaction conditions and the unexpected results achieved by their use.

U.S. Pat. No. 4,212,989, issued to Isshiki et al., on July 15, 1980, describes a process for producing carboxylic acids or their esters by reacting an alcohol or an ether with carbon monoxide using a Group VIII metal catalyst and an iodine promoter. The reference contains no disclosure or suggestion of the production of organic carboxylic acids employing a specific rhodium complex under mild reaction conditions.

British Patent Specification No. 1,286,224, issued Aug. 23, 1972 to Wakamatsu et al., relates to the reaction of methyl formate with carbon monoxide in contact with a rhodium catalyst and a halogen promoter to produce acetic acid. It contains no recognition of the distinct advantages achieved with the use of the instant specific rhodium complex.

British Patent Specification No. 1,293,193, issued Oct. 18, 1972 to Japan Gas-Chemical Company, Inc., relates to the direct conversion of formic acid esters to the corresponding carboxylic acids, in the presence of carbon monoxide, a catalyst that is a Group IIb or VIII metal and an organic polar solvent. It does not disclose use of the specific rhodium complexes of this invention.

British Patent Specification No. 1,584,740, issued Feb. 18, 1981 to Air Products relates to the production of acetic acid at more extreme reaction conditions using a different ligand, shown by us to be ineffective under the mild reaction conditions of this invention.

Frequently, as shown above, typical prior art processes employing rhodium catalyst to produce acetic acid, require rather harsh reaction conditions of temperature and pressure to obtain satisfactory yields of products. Such reaction conditions require use of expensive reactors, engender excessive energy cost, often lead to undesired by-products and cause excessive corrosion problems.

SUMMARY OF THE INVENTION

A process and catalyst system for the production of organic carboxylic acids has been discovered. The process can produce acids of the formula RCOOH, wherein R is a monovalent hydrocarbyl group, and preferably an alkyl group having 1 to 3 carbon atoms. The process includes the catalytic reaction of an alcohol of the formula ROH and carbon monoxide in contact with a homogeneous catalyst system at mild reaction conditions.

The catalyst system consists essentially of rhodium metal atom and a phosphorus containing ligand in which there is present at least one oxo (=O) oxygen atom attached to a phosphorus atom or a carbon atom to form a Z group and the

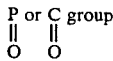

in said Z group is located at least one carbon atom removed and preferably from 2–4 carbon atoms removed from the phosphorus atom of the molecules represented by the formulas

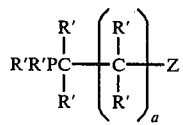 (V)

or

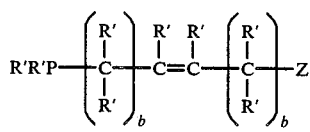 (VI)

and a halogen-containing compound as a promoter, wherein R' can be the same or different and is hydrogen or unsubstituted or substituted (for example; halogen, nitro, amino, and the like) aryl, aralkyl or alkaryl having from 6 to 10 ring carbon atoms and an alkyl moiety of the aralkyl or alkaryl group has from 1 to 10 carbon atoms and preferably 1 to 4 carbon atoms; or alkyl having from 1 to 10 carbon atoms and preferably 1 to 4 carbon atoms; and wherein 1 or more of said R' groups can be substituted with a Z group but not more than 3 of said R' groups in the molecule are so substituted; a is an integer from 0–4; b is an integer from 0–3; and Z is a member selected from the group consisting of

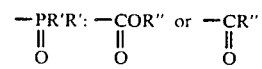

wherein R" is R' or —H.

The reaction conditions are mild, usually at reaction temperatures less than about 130° C. and at reaction pressure less than about 250 psig.

Under catalytic conditions it is understood that a novel monocarbonyl rhodium complex of the formula A:

 [A]

wherein X is halogen and R' and Z are as before, and wherein G represents the two

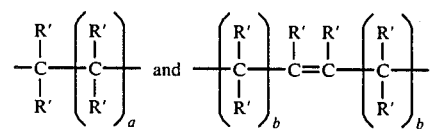

groups of formulas and is formed in situ.

The novel rhodium complex of the invention has been synthesized, isolated and characterized. The synthesized rhodium complex may be prepared in advance and used in place of the in-situ formed catalyst.

The Formula A rhodium complex is understood to be subject to the addition of a second mole of carbon monoxide to form a second catalytic dicarbonyl rhodium complex of Formula B and having the general formula:

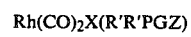 [B]

The Formula B rhodium complex can be prepared in advance of the process rather than being formed in si-situ from Formula [A].

DESCRIPTION OF THE INVENTION

In the catalytic reactions of synthesis gas or carbon monoxide in processes to produce oxygenated organic compounds there are several criteria required of the catalyst. The catalyst must be as stable as possible, it should have a high activity or conversion rate, and it should have as high a selectivity for the desired product as possible.

Stability of the catalyst relates to how long the catalyst remains functional before either breaking down or losing its catalytic effect.

Activity or conversion rate relates to the amount of reactants the catalyst converts to product per unit of time, generally expressed in g. mole per liter per hour (g mole/l/hr) or mole per hour (Mhr$^{-1}$).

Selectivity relates to the quantity of desired product produced, generally expressed in mole percent, based on the total amount of both desired products and undesired products produced.

The goal to be achieved is high values for all three criteria and continued efforts are being made to find new catalyst compositions to reach this goal without having a significant detrimental effect on the overall process. Toward this goal the prior art has developed catalyst systems containing a wide variety of metal atoms, promoters and activators, in many cases with diverse other components added. Though these catalyst systems are effective they usually require rather harsh reaction conditions and, accordingly, improvement is always desirable. Other factors having an impact on the process are the reaction temperature and reaction pressure. In the past it was generally thought necessary to increase these variables to improve oerall selectivity and conversion.

The present invention is based on the unexpected and unpredictable discovery that the herein defined rhodium-catalyst systems which contain the specifically defined ligands produce organic acids from alcohols and carbon monoxide at unexpected high efficiency, selectivity and conversion rate at mild reaction conditions. Optionally, a solvent and/or diluent can also be present.

In the process of our invention certain alcohols are reacted with carbon monoxide in the presence of the inventive catalyst system. This system produces commercially desirable organic acids at unexpectedly high efficiency, conversion rate and selectivity, with a minimum of by-products and under mild reaction conditions. The overall reaction that occurs in the production of acids is theoretically:

$$ROH + CO \rightarrow RCOOH$$

In the above formula; R may be a monovalent hydrocarbyl group and preferably, an alkyl group having from 1 to 3 carbon atoms and, most preferably, 1 carbon atom. The R group can be linear or branched and it can be unsubstituted or substituted with groups which will not have an adverse effect on the reaction. Among the suitable alcohols are methanol, ethanol and the propanols, with the preferred one being methanol.

The rhodium component of the catalyst system can be supplied from any number of sources, many of them are known to those of ordinary skill in the art. Thus, it is not necessary for an understanding thereof to specifically enumerate every suitable type and every specific compound since any of the known rhodium compounds can be used.

The essential rhodium component of the catalyst system of the present invention may be provided by introducing into the reaction zone a compound of rhodium or may be provided by introducing into the reaction zone, rhodium. Among the materials which may be charged to the reaction zone to provide the rhodium component of the catalyst system of the present invention are rhodium metal, rhodium salts and oxides, organo rhodium compounds, coordination compounds of rhodium, and the like. Specific examples of materials capable of providing the rhodium constituent of the catalyst system of the present invention may be taken from the following non-limiting partial list of suitable materials.

$RhCl_2$
$RhBr_2$
$RhI_2$
$RhCl_3.3H_2O$
$RhBr_3.3H_2O$ 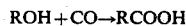 $Rh_2(CO)_4Cl_2$
$Rh_2(CO)_4Br_2$
$Rh_2(CO)_4I_2$
$Rh_2(CO)_8$
Rh metal
$Rh(NO_3)_3$
$[(n-C_4H_9)_4N][Rh(CO)_2X_2]$ where $X=Cl-$, $Br-$, $I-$
$[(n-C_4H_9)_4As]_2[Rh(CO)_2Y_4]$ where $Y=Cl-$, $Br-$, $I-$
$[(n-C_4H_9)_4P][Rh(CO)I_4]$
$Rh_2O_3$
$[Rh(C_3H_4)_2Cl]_2$
$K_4Rh_2Cl_2(SnCl_2)_4$
$K_4Rh_2Br_2(SnBr_3)_4$
$K_4Rh_2I_2(SnI_2)_4$ The rhodium metal atom concentration can vary over a wide range. Enough metal atom must be present to achieve reasonable reaction rates; however, an excess may, on occasion, result in undesired by-products formation.

The mole ratio of rhodium atom to alcohol can vary from 1:25 to 1:20,000, preferably range is from about 1:40 to 1:1000, with the most preferred range being from about 1:100 to 1:500. The amount used is not a critical feature in this invention and higher rhodium concentrations are acceptable but are influenced by economic considerations.

In general the rate of reaction increases with increasing rhodium concentration. For most purposes it is sufficient to employ a rhodium concentration from about 0.0001 to 1 mole per liter, preferably from about 0.01 to 0.1 mole per liter, although higher or lower concentrations may be utilized, depending, in part, upon economic considerations.

The second component of the catalyst system is a halide containing compound as a promoter.

The halide component of the catalyst can be a halogen compound containing iodine, bromine or chlorine or two or more of the same, or the elemental halogen per se, or any mixtures of compounds and/or elements. Their identities are well known to those of ordinary skill in this art.

The preferred halogen compound is iodine or inorganic or organic compounds containing the iodine atom. As indicated, the suitable halogen compounds are well known to those of average skill in this art and a complete listing is not necessary for their comprehension.

Illustrative thereof there can be mentioned barium iodide, hydriodic acid, cobalt iodide, potassium iodide, lithium iodide, sodium iodide, calcium iodide, ammonium iodide, methyl iodide, ethyl iodide, propyl iodide, 2-ethylhexyl iodide, n-decyl iodide, acetyl iodide, propionyl iodide; the organic ammonium iodides of the formula $(R''')_4NI$ and the organic phosphonium iodides of the formula $(R''')_4PI$ in which $R'''$ is alkyl, saturated or unsaturated, substituted or unsubstituted, having from 1 to about 10 carbon atoms or aryl, unsubstituted or substituted, having from 6 to 10 ring carbon atoms such as trimethyl ammonium iodide, tetraethyl ammonium iodide, tetra-2-ethylhexyl ammonium iodide, tetraphenyl ammonium iodide, tetramethyl phosphonium iodide, tetra-2-ethylhexyl phosphonium iodide, tetrapropyl phosphonium iodide, methyltriphenyl phosphonium iodie, and the like; methylammonium iodide, tri-p-tolyl-ammonium iodide, decylammonium iodide, ethylphosphonium iodide, triphenyl-phosphonium iodide, tricyclohexylphosphonium iodide, tri-p-tolylphosphonium iodide, and the like. Also useful are bromine and its corresponding compounds and chlorine and its corresponding compounds. Any source of halogen atom can be used provided that it does not have a deleterious effect on the reaction.

The amount of halogen charged is dependent upon the amount of rhodium employed. The halogen: rhodium mgm-atom ratio is generally from about 0.1:1 to 200:1, although greater or lesser amounts can be employed. It is prefered to employ a ratio from about 1:2 to about 100:1 and, most preferably, from about 1:1 to about 75:1.

The third component of the catalyst system is a phosphorus-containing ligand of the formula R'R'PGZ, wherein R' and G are as previously defined, and Z is selected from the group

In a first embodiment, the phosphorus-containing ligand has the general formula I:

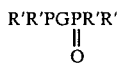

wherein R' and G are as before. The R' groups can be alike, different or mixed. Typical ligands of this embodiment include:

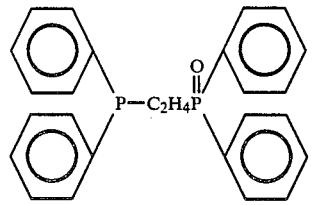     (1)

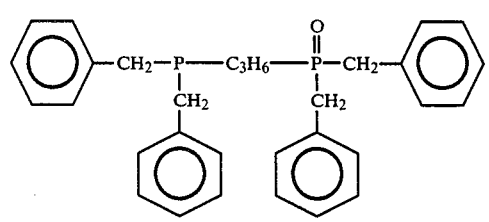     (2)

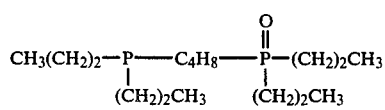     (3)

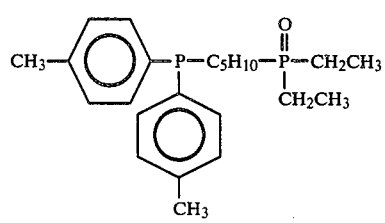     (4)

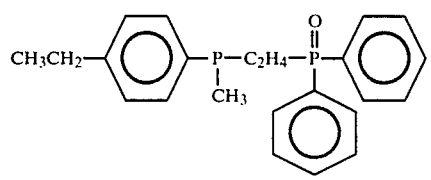     (5)

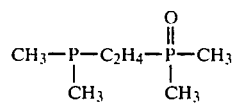     (6)

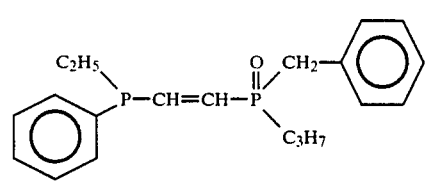     (7)

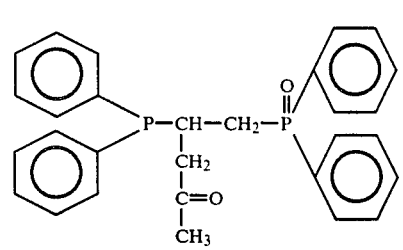     (8)

An especially preferred ligand of Formula (I) is

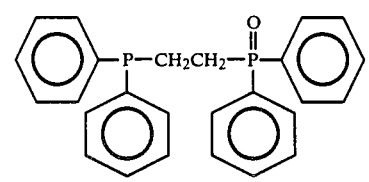

In a second embodiment the phosphorus-containing ligands have the general formula (II):

R'R'PGC(O)OR"

and in third embodiment the phosphorus-containing ligands have the general formula III:

wherein R' and G are as before; and R" is R' or —H.
Typical examples of formula II compounds include:

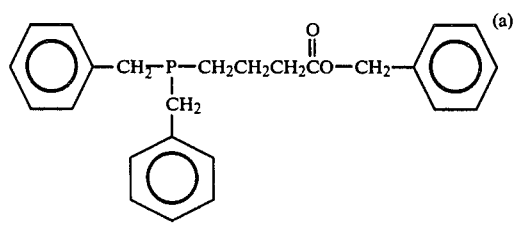     (a)

-continued

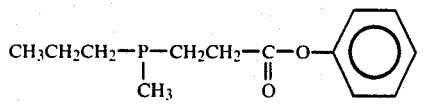
(b)

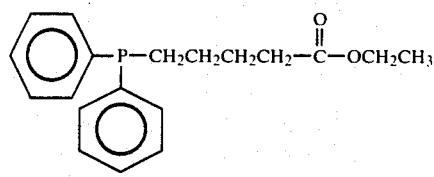
(c)

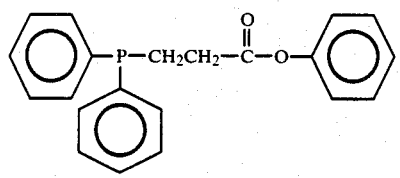
(d)

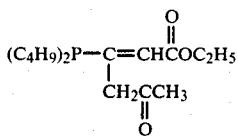
(e)

Typical examples of formula (III) compounds include:

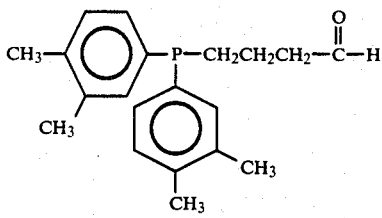
(f)

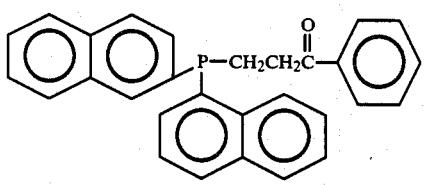
(g)

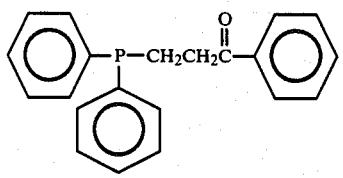
(h)

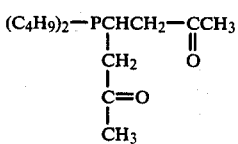
(i)

It has been found that conventional ligands such as $ER_3$ (E=P, N, As and R=organic moiety) and chelating agents, such as $R'R'P(CH_2)_nPR'R'$ tend to deactivate the catalyst system at low temperature and pressure.

It is believed important that the oxo (O=) group of the —P(O)—; —C(O)O— or —C(O)— moiety of Z may be capable of becoming bonded to the rhodium atom.

The reactive rhodium complex of formula A can be generally prepared and isolated by the typical reaction involving the dissolution of $[Rh(CO)_2Cl]_2$, or any other halide compound of this formula, in an inert solvent, such as dichloromethane, benzene, toluene and like, under inert atmospheric conditions. A stoichiometric amount of phosphine, based on the rhodium content, is added, and the mixture is stirred at a temperature of from about 0° C. or less up to the boiling point of the mixture, or higher. The reaction can be carried out at subatmospheric, atmospheric or superatmospheric pressure. The temperature and pressure are not critical.

Stirring is continued until the reaction is complete and this, as is obvious, will be dependent upon the specific reactants employed, reaction conditions used and the size of the batch. At completion of the reaction, one can, if so desired, separate the complex from the diluent using conventional procedures.

The structure of the formula A complex, identified herein as [A'] is believed to be (schematically) as follows:

[A']

wherein R', X and G are as before and Z' is —P—R'R'; —COR" or —CR" and wherein R" is R' or —H. The formula A complex may be formed in either the cis- or trans-geometrical isomer, wherein the X— and OC— moieties in complex A' are as they appear or are reversed.

Analysis to date of complex A' by NMR and IR has demonstrated the cis-isomer as the form present at room temperature.

In the catalytic reaction for the production of the carboxylic acid and the catalyst complex can be prepared and then added to the reactor or it can be formed in-situ during the reaction.

Carbon monoxide may be combined with Formula A complexes to form Formula B complexes. That complex may be represented (schematically) by Formula B' as follows:

[B']

wherein X, R', G and Z are as before.

If desired, Formula B complexes may be prepared in advance of the process by the carbonylation of Formula A complexes or the like. Formula B complexes have not yet been isolated, but, from spectral analyses of the reaction mixture appear to have the indicated structure. Other procedures which will be apparent to those skilled in this art may also be utilized to make Formula B complexes.

The concentration of ligand charged to the catalytic reaction can be varied from a molar ratio of ligand to rhodium of from about 5:1 to 1:5, preferably from 2:1 to 1:2 and most preferably about 1:1.

The reaction is carried out at a mild reaction temperatures, up to about 130° C. and preferably from about 40° C. to 120° C. and, most preferably, from 60° C. to 110° C.

The reaction pressure employed is much milder than those generally employed. The pressure of the reaction generally is up to about 250 psig and, preferably, from 50 psig to 150 psig.

The reaction time varies depending upon the reaction parameters, reactor size and charge, and the individual components employed at the specific process conditions. The reaction can be a batch or continuous reaction.

The process may be carried out in any convenient equipment, for example, either a glass pressure bottle (Fisher Porter Bottle ®) or in a 300 c.c. reaction autoclave. In the case of the glass bottle, degassed alcohol, as $CH_3OH$, containing a rhodium source; for example $[Rh(CO)_2Cl]_2$, and a phosphorus containing ligand, i.e. R'R'PGP(O)R'R', in the desired amounts were added under CO atmosphere to the bottle. Next a promoter, such as $CH_3I$, was added and the bottle was sealed by means of a valve and pressurized to 15 psig CO. The bottle was then heated to the desired reaction temperature at which point the pressure was adjusted to the reported value with CO. The bottle was repressurized after every 10 psig uptake.

The following procedures were used with a 300 cc Hasteloy ® steel autoclave reactor equipped with temperature and pressure sensing means, electrical heating means, an internal cooling coil, magnetically driven agitator and inlet and outlet means for introducing and removing components from the reactor. Prior to charging the reactants the autoclave was washed with methanol at 100° C. under a syn gas pressure of 500 to 1,000 psig by agitating for 30 minutes. The autoclave was drained, rinsed with dry acetone, and dried with nitrogen. The liquid components were charged to the cleaned autoclave first and then the solid components were added and stirred. The autoclave was closed, purged with carbon monoxide and then pressurized to the desired pressure, usually 20 to 30 psig with carbon monoxide. The autoclave contents were heated to the selected temperature generally between 50° and 100° C. with agitation (usually 750 rpm), in about 45 minutes. After the desired temperature was reached, the reaction was allowed to consume carbon monoxide for the time period indicated, usually from ½ to 5 hours. During this time the pressure was maintained by addition of carbon monoxide, as needed.

At the end of the reactor run, the contents were cooled, generally to about 10° C. A vapor phase sample was taken for gas chromatography analysis: the gas phase was vented through two dry-ice acetone traps and then through a 10 liter saturated solution of calcium hypochlorite to remove metal carbonyls, if formed. The reactor was pressurized three times with nitrogen, 90 psig, and vented through the same system.

The residual reactor contents were dumped into a chilled pressure bottle and sealed. Subsequent analysis was performed using a Hewlett-Packard Model 5880 gas chromatograph equipped with a one-eighth inch diameter by ten feet long column packed with Chromosorb 101 or a Varian 3700 gas chromatograph equipped with a SUPELCO DB 1701 30M capillary column.

The following examples serve to further illustrate this invention.

EXAMPLE 1

A Fisher Porter Bottle ® was charged with the following components:

| | |
|---|---|
| $[Rh(CO)_2Cl]_2$ | 0.09 gm (0.46 millimoles) |
| $Ph_2PCH_2CH_2P(O)Ph_2$ | 0.2 gm (0.48 millimoles |
| $CH_3I$ | 1.10 gm |
| $CH_3OH$ | 5.5 gm |

In the ligand formula, Ph represents a phenyl group. The bottle was sealed, pressured to 15 psi CO, then heated to 80° C. At 80° C. the pressure was adjusted to 80 psi with CO and the bottle was repressurized after every 10 psig CO uptake. The reaction was carried out for 3.0 hr. The products and their approximate amounts were as follows (excluding water):

| Product | Moles |
|---|---|
| Methanol | 0.018 |
| Methyl iodide | 0.012 |
| Methyl acetate | 0.057 |
| Acetic acid | 0.038 |

No other products were detected. The calculated rate to acetic acid (including methyl acetate equivalents) is 4.5 $MHr^{-1}$.

Similar results are obtained when other rhodium sources are substituted; such as $Rh_2(CO)_4Br_2$, $Rh(CO)_2AcAc^*$, $K_4Rh_2I_2(SnI_2)_4$, $[(n-C_4H_9)_4N][Rh(CO)_2I_2]$.

*AcAc=acetyl acetonate

EXAMPLE 2

Six runs were carried out in accordance with Example 1, except $Ph_2PCH_2CH_2P(O)Ph_2$ was not utilized. In each run the rhodium concentration was 0.071M; $CH_3I$:Rh ratio was 17:1; temperature was 80° C. and total operating pressure was 80 psig. The rate is in moles per hour ($Mhr^{-1}$). The results are summarized in Table 1.

TABLE 1

| Catalyst Precursor | Rate $Mhr^{-1}$ |
|---|---|
| (a) $[Rh(CO)_2Cl]_2$ | 0.05 |
| (b) $Rh(CO)_2AcAc$ | 0.1 |
| (c) trans-$Rh(CO)I(PPh_3)_2$ | 0.05 |
| (d) trans-$Rh(CO)I(Ph_2CH_3P)_2$ | 0.07 |
| (e) $[Rh(CO)_2Cl]_2$ + $2Ph_2PCH_2CH_2PPh_2$ | 0.0 |
| (f) $[Rh(CO)_2Cl]_2$ + $2Ph_2P(O)CH_2CH_2P(O)Ph_2$ | 0.03 |

Runs (a) and (b) are similar to those in U.S. Pat. No. 3,769,329 and show that at low temperature and low pressure, the productivities are very low. Runs (c) and (d) are similar to U.S. Pat. No. 4,212,989 and show addition of $ER_3$ is not beneficial. Run (e) is analogous to GB No. 1,584,740 which, under our conditions, is totally inactive. Run (f) demonstrates that the bis-oxide phosphine ligand $Ph_2P(O)CH_2CH_2P(O)Ph_2$ is also ineffective.

EXAMPLE 3

Five runs were carried out according to Example 1 utilizing various $Ph_2P(CH_2)_nP(O)Ph_2$ ligands of formula I. The product distribution was similar to that of Example 1. Units of addition were in M/L (moles per liter). The results are summarized below:

| Run | [Rh]<sup>a</sup> M/L | [CH₃I] M/L | L | [L] M/L | Rate Mhr⁻¹ |
|---|---|---|---|---|---|
| 1 | 0.071 | 1.2 | Ph₂PCH₂P(O)Ph₂ | 0.071 | 0.1 |
| 2 | 0.071 | 1.2 | Ph₂P(CH₂)₂P(O)Ph₂ | 0.142 | 0.9 |
| 3 | 0.071 | 1.2 | Ph₂P(CH₂)₃P(O)Ph₂ | 0.071 | 2.6 |
| 4 | 0.071 | 1.2 | Ph₂P(CH₃)₄P(O)Ph₂ | 0.071 | 2.5 |
| 5 | 0.071 | 1.2 | Ph₂P(CH₂)₂COCH₂CH₃ | 0.071 | 2.7 |

<sup>a</sup>Rh charged as [Rh(CO)₂Cl]₂

The data demonstrates that for the ligand Ph₂P(CH₂)ₙP(O)Ph₂ a value of n=1 is deterimental for catalysis.

Similar results are found when a preferred complex A is subsituted for the in-situ formed catalyst.

EXAMPLE 4

A series of test runs was carried out in accordance with Example 1 except the amounts of CH₃I and [Rh(CO)₂Cl]₂, were varied. An amount of ligand was employed such that L:Rh=1:1. The results are summarized below.

| [Rh] M/L | [CH₃I] M/L | I:Rh Ratio | HoAc Rate Mhr⁻¹ |
|---|---|---|---|
| 0.07 | 1.23 | 17:1 | 2.3 |
| 0.07 | 2.47 | 35:1 | 4.8 |
| 0.07 | 4.58 | 65:1 | 7.5 |
| 0.07 | 9.17 | 130:1 | 7.7 |
| 0.14 | 4.58 | 33:1 | 13.3 |
| 0.14 | 9.17 | 65:1 | 19.0 |

The composition of the liquid product was similar to Example 1. All runs were at 80° C. reaction temperature and 90 psig reaction pressure.

These results demonstrate that by adjusting the catalyst ratios exceptionally high productivities are possible at low temperature and pressure.

When other promoters are substituted for CH₃I, such as hydriodic acid, ethyl iodide, trimethyl ammonium iodide, methyl bromide, methyl triphenyl phosphonium chloride and the like, similar results are obtained.

EXAMPLE 5

Several runs were carried out in the 300 cc autoclave in order to evaluate the effect of pressure. The autoclave was charged with the following components:

| | |
|---|---|
| [Rh(CO)₂AcAc] | 1.81 gm (7.0 mm) |
| Ph₂PCH₂CH₂P(O)Ph₂ | 2.89 gm (7.0 mm) |
| CH₃I | 15.2 ml (244 mm) |
| CH₃OH | 100 ml | mm = millimoles

The reaction temperature was maintained at 80° C. for each run. The composition of the liquid products was similar to Example 1. The results are summarized below:

| Operating Pressure Psig | HoAc Rate Mhr⁻¹ |
|---|---|
| 90 | 3.9 |
| 180 | 4.1 |
| 260 | 2.7 |
| 360 | 1.5 |
| 460 | 0.6 |

These results demonstrate an inverse dependence of the process on CO pressure, which is contrary to the results reported in the literature for other systems. When other ligands such as

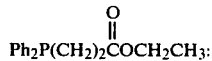

Ph₂P(CH₂)₂COCH₂CH₃:

(CH₃)₂P(CH₂)₃P(O)(CH₃)₂; (Tolyl)₂P(CH₂)₂-C(O)OCH₂CH₃ and (Benzyl)₂P(CH₂)₂P(O)(Benzyl)₂ are substituted for the ligand of Example 1, similar results are obtained.

EXAMPLE 6

The reaction was carried out in accordance with the procedure of Example 1 except that 1.0 ml of 57% HI was utilized in place of CH₃I. The liquid product composition was nearly identical to Example 1. The HoAc rate was 3.2 Mhr⁻¹.

EXAMPLE 7

The reaction was carried out in accordance with Example 1 except the temperature was maintained at 100° C. The liquid product composition was nearly identical to Example 1. The HoAc rate was 3.6 Mhr⁻¹.

When ethanol is substituted for methanol, the reaction rate is reduced and the acid produced is propionic acid.

EXAMPLE 8

Preparation of Complexes

A series of runs was performed using the following general procedure to produce the complexes of formulas A' and B'.

A solution of 2.5 millimoles (mm) of C₆H₅PCH₂P(O)(C₆H₅)₂ in 10 ml methylene chloride was added to a solution of 1.25 mm [Rh(CO)₂Cl]₂ in 10 ml methylene chloride. The mixture was allowed to stir for 10 minutes and the methylene chloride was removed under vacuum. The residual viscous oil was redissolved in 10 ml methylene chloride and the solvent evaporated again. This procedure was repeated three to four times.

The residue from the final evacuation was dissolved in 5 ml methylene chloride. Yellow crystals precipitated upon standing. The crystals were filtered, washed with methylene chloride and dried under vacuum. X-ray crystallographic analysis showed that the compound corresponds to:

cis-RhCl(CO)[(C₆H₅)₂PCH₂P(O)(C₆H₅)₂]·CH₂Cl₂, which contains a Rh to O bond. The infrared spectrum displayed a single intense band at 1990 cm⁻¹ due to the presence of coordinated CO to Rh in the complex.

The above procedure was followed exactly using (C₆H₅)₂P(CH₂)ₙP(O)(C₆H₅)₂; in which n was 2, 3 and 4 and for (C₆H₅)₂P(CH₂)ₙC(O)OC₂H₅ in which n was 2.

In all instances yellow crystals were recovered which gave infrared spectra similar to the first complex described above, having an intense band at 1990 cm$^{-1}$ indicating the formation of the similar structure. The complex products produced had the formulas:

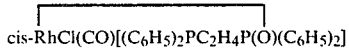
cis-RhCl(CO)[(C$_6$H$_5$)$_2$PC$_2$H$_4$P(O)(C$_6$H$_5$)$_2$]

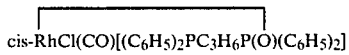
cis-RhCl(CO)[(C$_6$H$_5$)$_2$PC$_3$H$_6$P(O)(C$_6$H$_5$)$_2$]

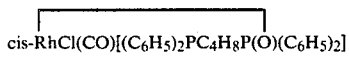
cis-RhCl(CO)[(C$_6$H$_5$)$_2$PC$_4$H$_8$P(O)(C$_6$H$_5$)$_2$]

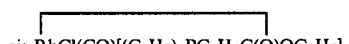
cis-RhCl(CO)[(C$_6$H$_5$)$_2$PC$_2$H$_4$C(O)OC$_2$H$_5$]

The dicarbonyl compounds of the above were prepared by reacting a portion of each of the above monocarbonyl compounds, respectively under CO pressure. Infrared spectra showed the formation of the dicarbonyl compounds had been achieved by the presence of two intense bands, typically at 2090 cm$^{-1}$ and 2010 cm$^{-1}$.

The dicarbonyl compounds had the formulas:

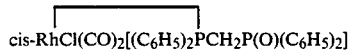
cis-RhCl(CO)$_2$[(C$_6$H$_5$)$_2$PCH$_2$P(O)(C$_6$H$_5$)$_2$]

cis-RhCl(CO)$_2$[(C$_6$H$_5$)$_2$PC$_2$H$_4$P(O)(C$_6$H$_5$)$_2$]

cis-RhCl(CO)$_2$[(C$_6$H$_5$)$_2$PC$_3$H$_6$P(O)(C$_6$H$_5$)$_2$]

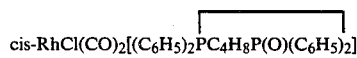
cis-RhCl(CO)$_2$[(C$_6$H$_5$)$_2$PC$_4$H$_8$P(O)(C$_6$H$_5$)$_2$]

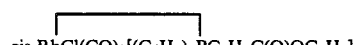
cis-RhCl(CO)$_2$[(C$_6$H$_5$)$_2$PC$_2$H$_4$C(O)OC$_2$H$_5$]

We claim:

1. A catalyst complex of formula: Rh(CO)X(R'$_2$PGZ) wherein X is halogen, R' is aryl, aralkyl, or alkaryl having from 6 to 10 ring carbon atoms and the alkyl moiety of said aralkyl or alkaryl group having from 1 to 10 carbon atoms or alkyl having from 1 to 10 carbon atoms and wherein 1 or more of said R' groups can be substituted with a Z group but not more than 3 of said R' groups in the molecule are so substituted; a is an integer from 0–4; b is an integer from 0–3; G represents the two groups:

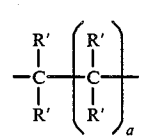

or

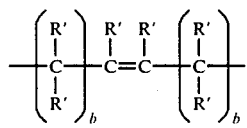

and Z ia a member selected from the group consisting of —P(O)R'R'; —C(O)R" or —C(O)OR", wherein R" is R' or —H.

2. A catalyst of formula: Rh(CO)$_2$X(R'$_2$PGZ) wherein X is halogen, R' is aryl, aralkyl or alkaryl having from 6 to 10 ring carbon atoms and the alkyl moiety of said aralkyl or alkaryl group having from 1 to 10 carbon atoms or alkyl having from 1 to 10 carbon atoms and wherein 1 or more of said R' groups can be substituted with a Z group but not more than 3 of said R' groups in the molecule are so substituted; a is an integer from 0–4; b is an integer from 0–3; G represents the two groups:

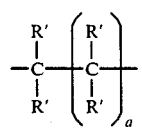

or

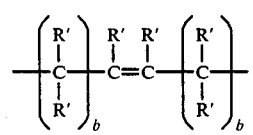

and Z is a member selected from the group consisting of —P(O)R'R'; —C(O)R" or —C(O)OR", wherein R" is R' or —H.

3. A catalyst complex as claimed in claim 1 of the formula:

cis-RhCl(CO)[(C$_6$H$_5$)$_2$PCH$_2$P(O)(C$_6$H$_5$)$_2$].

4. A catalyst complex as claimed in claim 1 of the formula:

cis-RhCl(CO)[(C$_6$H$_5$)$_2$PC$_2$H$_4$P(O)(C$_6$H$_5$)$_2$].

5. A catalyst complex as claimed in claim 1 of the formula:

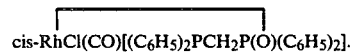
cis-RhCl(CO)[(C$_6$H$_5$)$_2$PC$_3$H$_6$P(O)(C$_6$H$_5$)$_2$].

6. A catalyst complex as claimed in claim 1 of the formula:

cis-RhCl(CO)[(C$_2$H$_5$)$_2$PC$_4$H$_8$P(O)(C$_6$H$_5$)$_2$].

7. A catalyst complex as claimed in claim 1 of the formula:

cis-RhCl(CO)[$(C_6H_5)_2PC_2H_4C(O)OC_2H_5$].

8. A catalyst complex as claimed in claim 2 of the formula:

cis-RhCl(CO)$_2$[$(C_6H_5)_2PCH_2P(O)(C_6H_5)_2$].

9. A catalyst complex as claimed in claim 2 of the formula:

cis-RhCl(CO)$_2$[$(C_6H_5)_2PC_2H_4P(O)(C_6H_5)_2$].

10. A catalyst complex as claimed in claim 2 of the formula:

cis-RhCl(CO)$_2$[$(C_6H_5)_2PC_3H_6P(O)(C_6H_5)_2$].

11. A catalyst complex as claimed in claim 2 of the formula:

cis-RhCl(CO)$_2$[$(C_6H_5)_2PC_4H_8P(O)(C_6H_5)_2$].

12. A catalyst complex as claimed in claim 2 of the formula:

cis-RhCl(CO)$_2$[$(C_6H_5)_2PC_2H_4C(O)OC_2H_5$].

* * * * *